US00PP24280P2

(12) United States Plant Patent
Hansen

(10) Patent No.: US PP24,280 P2
(45) Date of Patent: Mar. 4, 2014

(54) ***BAPTISIA* PLANT NAMED 'LEMON MERINQUE'**

(50) Latin Name: ***Baptisia* hybrid**
Varietal Denomination: Lemon Merinque

(75) Inventor: Hans Andrew Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 13/374,346

(22) Filed: Dec. 22, 2011

(51) Int. Cl.
*A01H 5/00* (2006.01)

(52) U.S. Cl.
USPC ..... Plt./263.1; Plt./226

(58) Field of Classification Search
USPC ..... Plt./263.1, 226
See application file for complete search history.

*Primary Examiner* — Susan McCormick Ewoldt
(74) *Attorney, Agent, or Firm* — Penny J. Aguirre

(57) ABSTRACT

A new cultivar of interspecific *Baptisia*, 'Lemon Merinque', characterized by its flowers that are yellow in color on erect flower stems with a charcoal colored overlay, its densely branched, uniform and upright plant habit and its vigorous growth rate.

2 Drawing Sheets

Botanical classification: *Baptisia* hybrid.
Cultivar designation: 'Lemon Merinque'.

BACKGROUND OF THE INVENTION

The present invention relates to a new and distinct cultivar of hybrid *Baptisia* plant, botanically an interspecific hybrid in origin and known as *Baptisia* 'Lemon Merinque' and will be referred to hereafter by its cultivar name, 'Lemon Merinque'. The new cultivar represents a new false indigo, an herbaceous perennial grown for ornamental landscape use.

The new invention arose from an ongoing controlled breeding program in Waseca, Minn. The breeding program was established by the Inventor in 1998 with the goal of developing *Baptisia* hybrids with unique flower colors and plant habits.

'Lemon Merinque' was derived from a cross made in 2003 between an unnamed plant of *Baptisia sphaerocarpa* as the female parent and an unnamed plant selection of *Baptisia alba* var. *alba* as the male parent. 'Lemon Merinque' was selected in 2007 as a single unique plant amongst the resulting seed progeny.

Asexual reproduction of the new cultivar was first accomplished by stem cuttings in June of 2008 in Zeeland, Mich. under the direction of the Inventor. The characteristics of this cultivar have been determined to be stable and are reproduced true to type in successive generations.

SUMMARY OF THE INVENTION

The following traits have been repeatedly observed and represent the characteristics of the new cultivar as observed for five years in Waseca, Minn. These attributes in combination distinguish 'Lemon Merinque' from other varieties of *Baptisia* known to the Inventor.

1. 'Lemon Merinque' exhibits flowers that are light yellow in color.
2. 'Lemon Merinque' exhibits blue-green foliage.
3. 'Lemon Merinque' has an upright and uniform plant habit with numerous flower stems suffused with a charcoal colored overlay.

4. 'Lemon Merinque' is hardy in U.S.D.A. Zones 4 to 8.

In comparison to the female parent, *Baptisia sphareocarpa*, 'Lemon Merinque' has light yellow flowers whereas *Baptisia sphaerocarpa* has dark yellow colored flowers, 'Lemon Merinque' is also taller with an upright, more uniform and less spreading plant habit, and has longer inflorescences. In comparison to the male parent, *Baptisia alba* var. *alba*, 'Lemon Merinque' has light yellow flowers and more vigorous and branching plant habit, whereas *Baptisia alba* var. *alba* has white flowers and a less vigorous habit. The closest comparison plant is *Baptisia* 'Carolina Moonlight' (not patented); it is also an interspecific hybrid, however it differs in having green colored stems instead of charcoal colored stems. 'Lemon Merinque' can also be compared to *Baptisia* 'Solar Flare' (U.S. Plant Pat. No. 20,408), an intespecific hybrid with light yellow colored flowers. 'Solar Flare' differs from 'Lemon Merinque' in having a much larger plant habit (maturing to 6 feet in width), in having green stems rather than charcoal colored stems, and in having flowers that mature to orange-brown in color.

BRIEF DESCRIPTION OF THE DRAWING

The accompanying colored photographs illustrate the overall appearance and distinct characteristics of the new *Baptisia*. The photographs were taken of plants and plant parts of a plant five years in age as grown outdoors in Waseca, Minn.

The photograph in FIG. 1 is a view of 'Lemon Merinque' in bloom and illustrates the uniform upright habit and the abundance of flowering stems.

Figure 1:
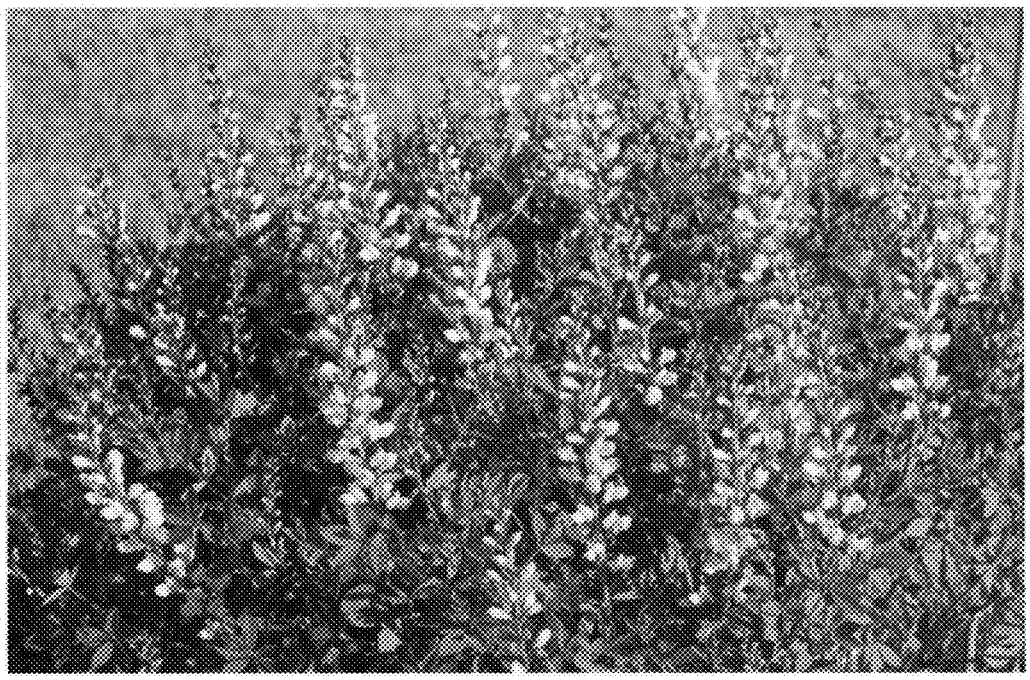
Figure 2:
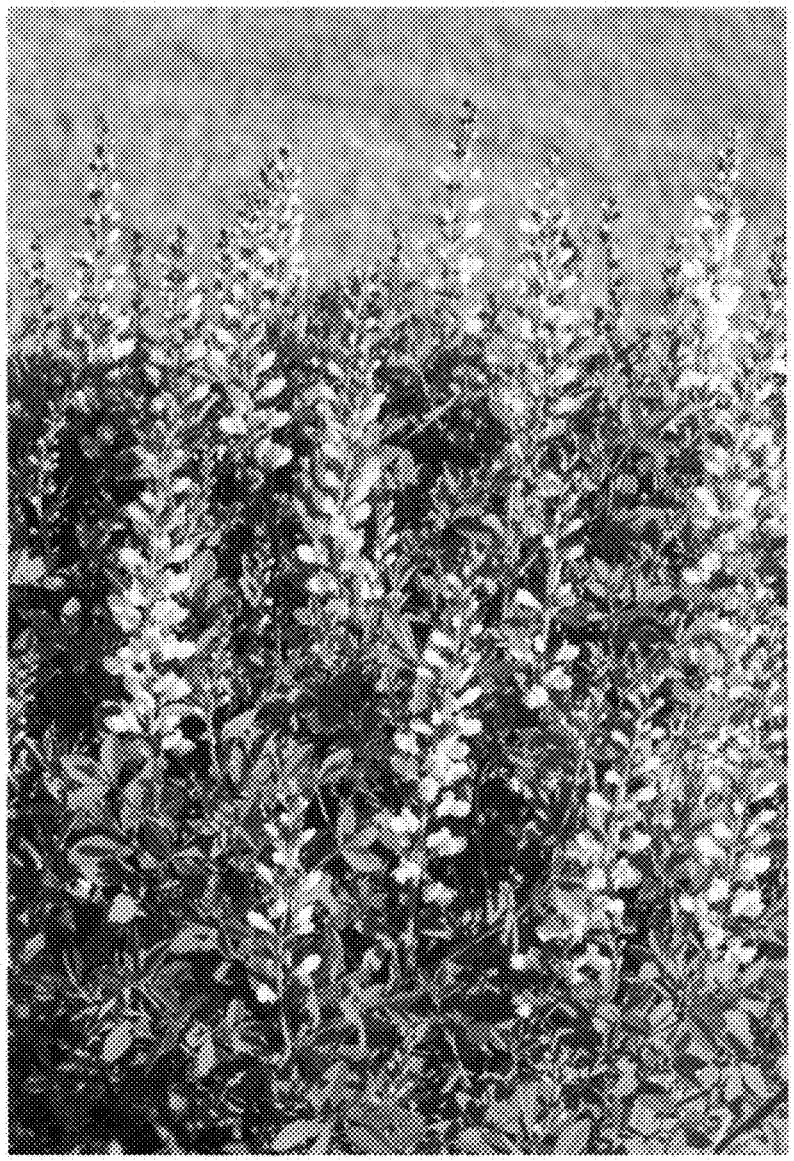

The photograph in FIG. 2 is a close-up view of inflorescences of 'Lemon Merinque'.

The colors in the photographs may differ slightly from the color values cited in the detailed botanical description, which accurately describe the colors of the new *Baptisia*.

DETAILED BOTANICAL DESCRIPTION OF THE PLANT

The following is a detailed description of 5 year-old plants of the new cultivar as grown outdoors in a trial plot in Waseca, Minn. The phenotype of the new cultivar may vary with variations in environmental, climatic, and cultural conditions, as it has not been tested under all possible environmental conditions. The color determination is in accordance with The 2001 R.H.S. Colour Chart of The Royal Horticultural Society, London, England, except where general color terms of ordinary dictionary significance are used.

General description:

*Blooming period.*—June 6th through June 25th in Waseca, Minn.

*Plant habit.*—Upright.

*Height and spread.*—Reaches 89 cm width and 86 cm in height.

*Hardiness.*—U.S.D.A. Zones 4 to 8.

*Culture.*—Prefers well-drained to medium moist soils in full sun, tolerant to lean soils and drought.

*Diseases and pests.*—No susceptibility to diseases or pests has been observed.

*Root description.*—Deep rooted, fibrous.

Growth and propagation:

*Propagation.*—Stem cuttings is the preferred method of propagation, tissue culture is also possible.

*Growth rate.*—Very vigorous relative to other *Baptisia* species and cultivars.

Stem description:

*Branch habit.*—Well branched; average of 22 branches with an average of 5 secondary branches, and 3 to 4 tertiary branches per secondary branch.

*Stem size.*—Main stem; average of 80 cm (including peduncle) in length and 7 mm in width (9 mm at base), secondary; average of 33 cm in length and 4 mm, tertiary; an average of 10 cm in length and 2 mm in width.

*Stem shape.*—Oval.

*Stem color.*—144A to 144B lightly suffused with N186B.

*Stem surface.*—Hairless, satiny but slightly glaucous with vertical ridges.

Foliage description:

*Leaf shape.*—Fan-shaped in overall outline.

*Leaf division.*—3-palmate.

*Leaf internode.*—Foliage begins 38 cm from base, an average of 4.7 cm on main stem and 4 cm on secondary branches.

*Leaf size.*—About 4.9 cm in length and 8.5 cm in width.

*Leaf quantity.*—About 108 per stem (including all branches).

*Leaflet shape.*—Oblanceolate.

*Leaflet base.*—Cuneate.

*Leaflet apex.*—Broadly acute and minutely retuse.

*Leaflet venation.*—Pinnate pattern, color on the upper surface 146C and lower surface with the mid rib of lower surface 147D.

*Leaflet margins.*—Entire.

*Leaf attachment.*—Petiolate.

*Leaf arrangement.*—Alternate.

*Leaflet surface.*—Glabrous and slightly glaucous on upper and more glaucous on lower surface.

*Leaflet color.*—Newly expanded upper and lower surface; color between 144A and 137C, mature; upper surface 137A and lower surface N138B.

*Leaflet size.*—An average of 4.7 cm in length and 2.2 cm in width.

*Petioles.*—Average of 9 mm in length and 2 mm in width, clasping to stem at mature nodes, 146B in color and lightly suffused with N186B, surface is glabrous and satiny.

*Stipules.*—Not present at all nodes, narrowly lanceolate in shape, reflexed to stem, base is truncate to stem, apex is apiculate, average of 6 mm in length and 5 mm in width on mature leaves, 137C in color on upper surface and 138A on lower surface.

Flower description: Bright yellow with dark grey calyx.

*Inflorescence type.*—Terminal racemes of pea-like flowers on main with smaller racemes on secondary branches, blooms from the base to the apex.

*Inflorescence size.*—Average of 27 cm in length and 5 cm in width at mid point.

*Lastingness of inflorescence.*—3 to 4 weeks.

*Flower size.*—About 2.4 cm in depth and about 1.5 cm in diameter.

*Flower fragrance.*—Faint.

*Flower number per inflorescence.*—About 40 to 50.

*Peduncle.*—Oval in shape, up to 30 cm in length and an average of 4 mm in width, 148A in color, surface is glabrous, satiny and slightly glaucous, flower internode length averages about 5 mm.

*Pedicel.*—About 5 mm in length, about 1.5 mm in width, oval in shape, 148A in color, glabrous and satiny surface.

*Flower buds.*—Kidney-shaped, about 1.9 cm in length and 8 mm in width, color of petal portion is a blend of 154B and 154C, calyx portion same as open flowers.

*Flower type.*—Papilionaceous, held at about a 45° angle.

*Calyx.*—Campanulate, about 9 mm in length and 5 mm in diameter, surface is glabrous and satiny, 148A in color and heavily suffused with 200A, persistent.

*Sepals.*—5, fused with the exception of apex of each, free portion is triangular in shape 3 mm in width and 4 mm in depth with an acute apex, 148A in color and heavily suffused with 200A.

*Corolla features.*—Papilionaceous (4 segments) with a keel, a banner and 2 lateral wings, lateral wings; obelliptic in shape, flared to expose keel, about 1.5 cm in length and 7 mm in width, color on outer surface 3B to 3C and inner surface 3D with the basal portion 157C, rounded apex, oblique base, keel; only partially visible, comprised of 2 segments surrounding reproductive organs, oblong (slightly oblique) in shape with rounded apex and oblique base, 2 cm in length and 9 mm in width, upper and lower surface are 1D in color with apex suffused with 1D, banner; orbicular in shape and partially reflexed, about 1.9 cm in length and 1.6 cm in width, upper surface 3D and lower surface lower surface is 3B to 3C with 3D near edges and markings of 200A near mid region, apex is rounded with a single notch, surface is glabrous on all sections and all petals have entire margins.

*Receptacle.*—Disk-shaped, gelatinous, 137B in color, about 3 mm in diameter and 1.2 mm in depth.

Reproductive organs:

*Gynoecium.*—1 Pistil, about 1.6 cm in length, 1.5 mm in width; style is 144D in color and 7 mm in length; stigma minute, too small to read color, ovary is superior with a stipe, 144A in color, 8.5 mm in length and 1.5 mm in width; stipe is 144D in color, 4 mm in length and 1 mm in width.

*Androcoecium.*—10 stamens, not united, 1.9 cm in length and <1 mm in width; filament is 1.8 cm in length, 1 mm in width and 145C in color; anther is dorsifixed, many amorphously shaped, about 1.5 mm in length and 1 mm in width and 13A in color, pollen is moderate in quantity and 17A in color.

*Fruit and seed.*—An inflated pod, technically a legume, about 20 to 25 produced per inflorescence (open pollinated), globose-oblong in shape, 1.9 to 2.2 cm in length and 9 to 11 mm in width; each with a short beak approximately 1 mm in length, color of outer surface when mature in September is a color between 201A and 202A, color of inner surface 200C to 200D in color, walls about 2 mm thick and woody at maturity, seed; 6 to 12 per fruit (open-pollinated), 165A in color, oval with the hilum side more or less straight, seed compressed to flattish, 4 mm in length, 3 mm in width, and 1.5 mm in thickness.

It is claimed:

1. A new and distinct cultivar of *Baptisia* plant named 'Lemon Merinque' as herein illustrated and described.

* * * * *